United States Patent [19]

Feduska et al.

[11] Patent Number: 5,045,169

[45] Date of Patent: Sep. 3, 1991

[54] SOLID OXIDE ELECTROLYTE ELECTROCHEMICAL OXYGEN GENERATOR

[75] Inventors: William Feduska, Edgeworth Boro; Arnold O. Isenberg, Pittsburgh, both of Pa.; Jack T. Brown, Bethesda, Md.

[73] Assignee: Westinghouse Electric Corp., Pittsburgh, Pa.

[21] Appl. No.: 474,899

[22] Filed: Feb. 5, 1990

[51] Int. Cl.$^5$ .................. C25B 9/04; C25B 15/08; H01M 8/18; H01M 8/04

[52] U.S. Cl. .................. 204/258; 204/260; 204/283; 204/284; 204/279; 204/291; 204/265; 204/266; 204/262; 429/21; 429/26; 429/31

[58] Field of Search ............... 204/260, 283, 284, 256, 204/258, 274, 263–266, 279, 291–292; 429/17, 19, 27, 31, 21, 26

[56] References Cited

U.S. PATENT DOCUMENTS

| | | | |
|---|---|---|---|
| Re. 28,792 | 4/1976 | Ruka et al. ..................... | 204/1 T |
| 3,460,991 | 8/1969 | White, Jr. ........................ | 136/86 |
| 3,525,646 | 8/1970 | Tannenberger et al. ........ | 136/86 |
| 3,668,010 | 6/1972 | Fally et al. ..................... | 429/31 |
| 4,395,468 | 7/1983 | Isenberg ......................... | 429/31 |
| 4,449,990 | 5/1984 | Tedford, Jr. .................... | 55/26 |
| 4,490,444 | 12/1984 | Isenberg ......................... | 429/31 |
| 4,609,362 | 9/1986 | Isenberg et al. ................ | 427/8 |
| 4,699,852 | 10/1987 | Yokoyama et al. .............. | 429/31 |
| 4,725,346 | 2/1988 | Joshi .............................. | 204/242 |
| 4,728,584 | 3/1988 | Isenberg ......................... | 429/31 |

Primary Examiner—Donald R. Valentine
Attorney, Agent, or Firm—Daniel P. Cillo

[57] ABSTRACT

An electrochemical device (10) capable of generating oxygen from air (23) upon application of an electrical current, is made containing a plurality of adjacent cells (12) and (12') electrically connected in series, where each cell contains optional support (22), inner, porous oxygen electrode (20), dense, solid oxide electrolyte (14) on top of the inner oxygen electrode, and outer, porous air electrode (16) on top of the electrolyte, where dense segments of interconnection material (18) are disposed between cells, the interconnection electrically connecting the outer air electrode from one cell to the inner oxygen electrode from an adjacent cell, where the device contains gas impermeable, dense, contacting segments of electrolyte (14) and interconnection material (18) and can contain two end portions at least one of which provides for oxygen delivery.

32 Claims, 3 Drawing Sheets

SOLID OXIDE ELECTROLYTE ELECTROCHEMICAL OXYGEN GENERATOR

BACKGROUND OF THE INVENTION

1. Field of the Invention

This invention relates to an oxygen generator, having series connected cells, that can produce very high purity oxygen, with the cells based on the use of: a dense, solid oxide electrolyte; porous oxygen electrodes; porous air electrodes; and dense, cell-to-cell interconnections, which oxygen generator is particularly useful in an oxygen concentration apparatus.

2. Description of the Prior Art

Small oxygen concentrators are usually based upon pressure swing, nitrogen adsorption systems which concentrate the oxygen from ambient air to deliver approximately 95% $O_2$ at about 3 liters of $O_2$/minute. U.S. Pat. No. 4,449,990 (Tedford) describes one such apparatus.

Although extremely reliable, these pressure swing adsorption units have certain disadvantages. They parasitically consume a major portion of the oxygen produced by back purging a standby tank of nitrogen adsorbent, in order to remove residual nitrogen, to rejuvenate the bed, prior to its next adsorption cycle. The units require timing and switching subsystems to activate a fixed time interval pressure swing in alternating between two nitrogen adsorption tanks. Also the nitrogen adsorbent can be rendered ineffective if exposed to excess humidity from the inlet air. In addition, purity is limited to approximately 95% $O_2$.

Other oxygen-nitrogen separation devices are known, and taught by U.S. Pat. No. Re. 28,792 (Ruka et al.), where in one embodiment of the invention, single, tubular $(ZrO_2)_{1-x}(R_yO_z)_x$ solid electrolyte, where R is selected from Ca, Ba, Sr, Y, La, Sc, Yb and Sm, is coupled with a first electrode of porous lanthanum-nickel oxide or porous calcium-lanthanum-manganese oxide and a second electrode of nickel-platinum, or, alternatively, with a metal selected from Pt, Pd, Rh, Ir or their alloys as electrodes. A D.C. power source is used to transfer oxygen through the electrolyte.

Oxygen removal from air by dissociation of 02 into oxygen ions at a porous electrode-solid electrolyte interface is taught in U.S. Pat. No. 4,725,346 (Joshi). There, electric current flows with oxygen ions through a tubular, nonporous, thin electrolyte selected from solid zirconium oxide, hafnium oxide, cerium oxide or bismuth oxide. Exterior, porous electrodes, deposited on the electrolyte, are either silver, alloys of silver, or mixtures of silver and conductive ceramic oxides. Cell operation is in a sealed enclosure at over 500° C. For medical oxygen generating devices, about 80% pure $O_2$ is produced.

Solid oxide electrolyte cells and configurations are well known, and taught in U.S. Pat. Nos. 4,395,468 and 4,490,444 (Isenberg), but there, air and fuel are fed into the apparatus to generate electricity. This design involves a loosely sealed generator housing, with long tubular cells, each utilizing a single yttria-zirconia solid electrolyte, coupled with a single nickel-zirconia or cobalt-zirconia cermet fuel electrode, and a single air electrode selected from, for example, doped or undoped $LaMnO_3$, $CaMnO_3$, $LaNiO_3$, $LaCoO_3$, $LaCrO_3$, and doped $In_2O_3$, and also including an oxide doped (Ca, Sr, Mg) lanthanum chromite interconnection film. A different, stacked configuration, using primarily the same materials is taught in U.S. Pat. No. 4,728,584 (Isenberg). There, annular interconnection members separate cells, and the outer electrode of one cell is electronically and physically segmented from the inner electrode of an adjacent cell. End caps are also utilized.

Banded, series connected, stacked cell, solid oxide electrolyte fuel cell configurations are also well known, and taught, for example in U.S. Pat. No. 3,460,991 (White) and U.S. Pat. No. 3,525,646 (Tannenberger et al.). The former patent utilizes a stabilized $ZrO_2$ solid electrolyte coupled with a first electrode selected from, for example, platinum, lithiated nickel oxide, and praseodymium cobaltate, and a second electrode selected from, for example, platinum, and nickel or silver in a mixture with conducting oxide material. Here, separate interconnections are not used between outer electrodes of one cell and inner electrodes of adjacent cells on the same tube. The latter patent utilizes a sealed conduit with an electrolyte of a ternary mixed oxide, such as, $ZrO_2+CaO+MgO$, a conductive wall material of nickel aluminide, coupled with a silver or nickel oxide/lithium oxide mixture as an outer electrode, and a supported inner electrode selected from, for example, iron, nickel, cobalt, copper, or their alloys. Here, electrolyte is disposed only on top of the base layer, not contacting the support.

The cells are shifted so that a conducting material disposed between electrolyte segments covers most of an insulating layer disposed completely between inner electrode segments.

White teaches a complex structure between cells that is not gas-impervious, since both overlapping electrodes are porous. Tannenberger et al. teach a complex arrangement of a minimum of six to seven cell components of dissimilar materials, and physical and chemical characteristics which makes the device extremely difficult to manufacture and operate in a reliable manner, especially with regard to gas tightness.

An alternate technology oxygen generator, overcoming state-of-the-art oxygen generator disadvantages in a system utilizing thin film technology, with the capability of producing high purity (99.9%) oxygen, and with the potential of being cost competitive, is needed. It is one of the objects of this invention to provide such a thin film oxygen generator.

SUMMARY OF THE INVENTION

Accordingly, the invention is characterized by an electrochemical device, capable of generating oxygen from air upon the application of an electrical current, where a plurality of adjacent electrochemical cells are electrically connected in series, each cell containing an inner, porous oxygen electrode; a dense, solid oxide electrolyte capable of transporting oxygen ions partly disposed on top of the inner electrode and partly disposed between inner electrodes of adjacent cells; an outer, porous air electrode disposed on top of the electrolyte; and separate, dense, electronically conductive segments of interconnection material disposed between adjacent cells, the interconnection electrically and physically connecting the outer air electrode from one cell to the inner oxygen electrode from an adjacent cell, said device having gas impermeable, dense, contacting segments of electrolyte and interconnection material between inner electrodes of adjacent cells.

In this gas impervious device, electrical current can be fed into and through the cells, where air can contact the outer air electrodes and electrolyte but cannot permeate through the dense contacting segments of electrolyte and interconnection material, and where oxygen from the air can be transported in ionic form across the electrolyte to provide oxygen gas within the generator device. The generator device is preferably of tubular design and contains two end portions, at least one of which provides for oxygen delivery.

In this device, preferably, the inner oxygen electrode of a first cell and the inner oxygen electrode of an adjacent cell are separated from each other and disposed on a porous support; interconnection material contacts part of the uncovered portion of the support next to the oxygen electrode of the adjacent cell and overlaps a portion of that oxygen electrode; and the solid electrolyte from the first cell continues beyond the end of the oxygen electrode of the first cell onto the remaining uncovered portion of the support, overlapping part of the interconnection. Thus, both electrolyte and interconnection material are disposed between inner electrodes of adjacent cells, and this is essential in this design to prevent gas leakage.

Most preferably, the inner, oxygen electrode contains a porous, sintered oxide, such as doped lanthanum manganite; the electrolyte contains dense stabilized zirconia; the outer, air electrode is constructed from a porous, metal-ceramic (cermet) material selected from the group consisting of platinum-zirconia, palladium-zirconia, and silver-palladium-zirconia, or a porous, sintered oxide selected from the group consisting of doped lanthanum manganite and doped lanthanum chromite; the interconnection contains a dense layer selected from the group consisting of platinum-zirconia, palladium-zirconia, silver-palladium-zirconia, palladium, platinum, palladium-silver, doped lanthanum manganite, and doped lanthanum chromite, with doped lanthanum manganite preferred.

The term "tubular" as used herein, is meant to include any axially elongated structural form having a closed cross-section. The term "air electrode" means that electrode which contacts ambient air on the outside of the generator and allows formation of oxygen ions from oxygen in the air, the term "oxygen electrode" means that electrode which allows formation of oxygen gas from oxygen ions and allows passage the oxygen gas into the interior of the generator, and the term "dense" means at least 95% of theoretical density.

The invention further resides in a method of making an electrochemical device capable of generating oxygen from air upon the application of an electrical current, characterized by the steps of: (1) supplying a tubular, porous support tube, (2) applying at least a first, inner oxygen electrode and a second, adjacent, inner oxygen electrode as discrete layers of porous material in the form of bands on the porous support tube, where the first oxygen electrode and the adjacent oxygen electrode are spaced apart from each other, (3) applying a discrete dense segment of electronically conductive interconnection material over part of the uncovered portion of the support tube between the spaced apart oxygen electrode bands, next to the second oxygen electrode and overlapping a portion of that oxygen electrode, (4) applying a discrete layer of dense, solid oxide electrolyte capable of transporting oxygen ions, in the form of a band over a part of the first inner oxygen electrode, continuing beyond the first oxygen electrode and contacting and covering the uncovered portion of the support between the spaced apart oxygen electrodes, overlapping part of the interconnection that contacts the second oxygen electrode but not contacting the second oxygen electrode, (5) applying a discrete layer of porous air electrode material in the form a band, over a part of the electrolyte band, starting a predetermined distance from the first end of the electrolyte band and continuing beyond the electrolyte and contacting the interconnection material segment which contacts the second oxygen electrode, providing a plurality of electrically connected cells, and (6) applying, at each end of the device, electrical terminals, and two end portions, at least one of the end portions providing for oxygen delivery, where the cells are electrically connected in series and the device has gas impermeable, dense contacting bands of electrolyte and segments of interconnection material.

This generator, driven by a D.C. power source, and operating at from 650° C. to 1,100° C. with preheated air, which can be unpressurized can extract as high as 99% pure $O_2$, at a rate of, for example, from 0.1 liters/minute to 10 liters/minute, from incoming air.

BRIEF DESCRIPTION OF THE DRAWINGS

In order that the invention will be more readily understood, the following description of preferred embodiments will now be described by way of example only, with reference to the accompanying, non-limiting drawings, in which.

DESCRIPTION OF THE PREFERRED EMBODIMENTS

Figure 1:
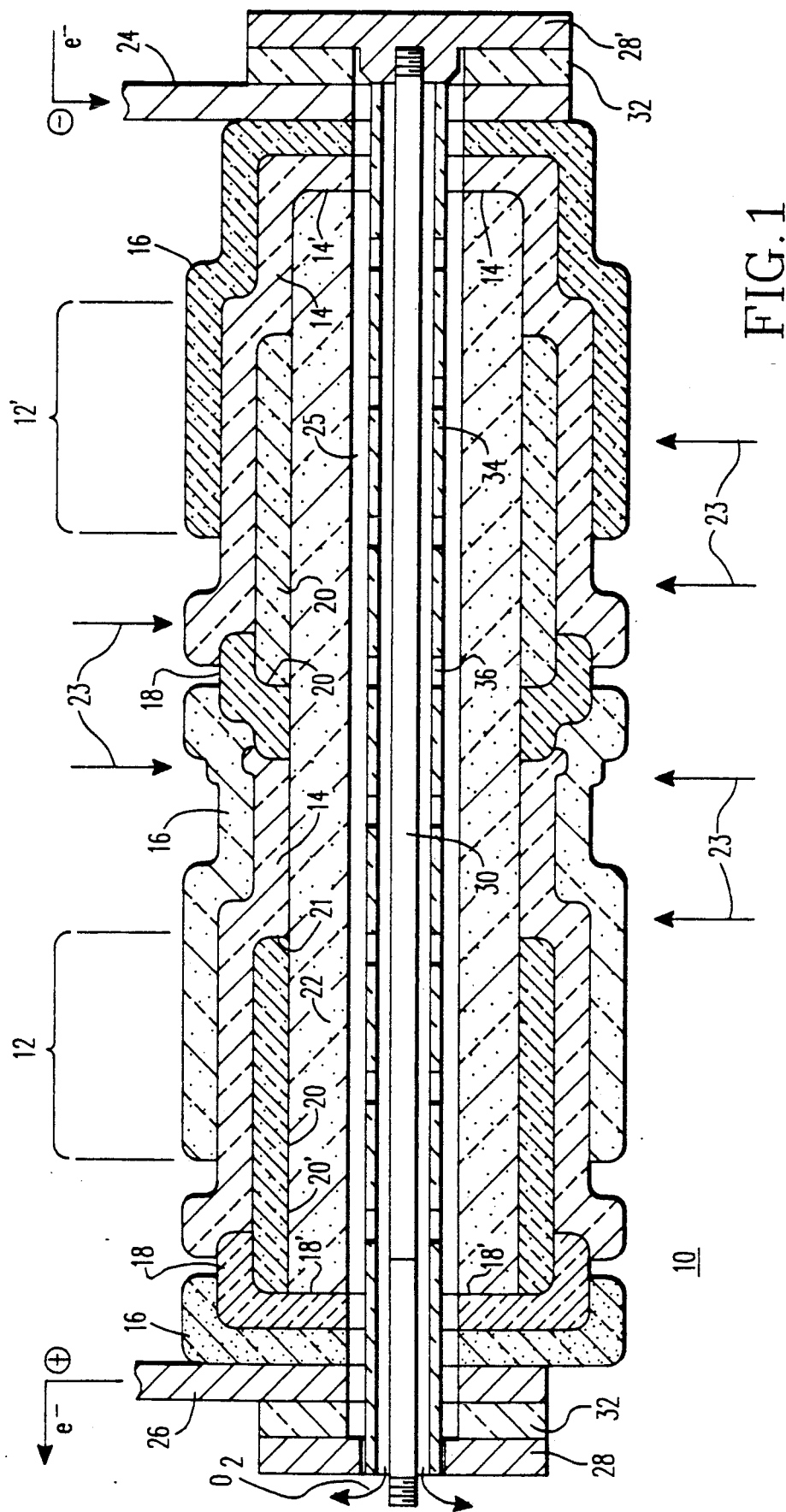
FIG. 1, which best illustrates this invention, is a plan view, partially in section, of one embodiment of a tubular, stepped, stacked, oxygen generator according to this invention, showing the cell configuration, end seal portions, power contacting connections, and a source of air.

Referring now to FIG. 1 of the Drawings, a high-temperature electrochemical device 10, useful as an oxygen generator is shown, having a closed cross-section, preferred tubular form, and comprising a plurality of adjacent electrochemical cells, the active lengths of which are shown as first cell 12 and adjacent cell 12', arranged end-to-end. These cells are electrically connected in series through continuous, spaced apart solid oxide electrolyte bands or segments 14, continuous, spaced apart air electrode bands 16, continuous, spaced apart interconnection segments 18, and continuous, spaced apart oxygen electrode bands 20.

Optional, porous support 22, which is preferably from 20% to 40% porous (80% to 60% of theoretical density), and which is generally used, as shown, supports oxygen electrodes 20, and the rest of the structure. Dense, solid electrolyte 14 is disposed on top of part of the inner oxygen electrode 20 starting a predetermined length from a first end 20' of each oxygen electrode. Outer porous air electrode 16 is disposed on top of part of the electrolyte 14 and in contact with air 23, which surrounds the generator body 10.

Electrical connection from cell to cell is made by a stacked configuration, where dense, preferably 100% dense, gas impervious, electronically conductive interconnection 18 is deposited over and contacts part of the uncovered portion of the support 22 next to the oxygen electrode 20 from cell 12′, and overlaps a portion of that oxygen electrode. Dense, gas impervious, ionically conducting, solid electrolyte 14 from first cell 12 is deposited on top of part of the inner, oxygen electrode 20 from cell 12, continuing beyond the end 21 of the oxygen electrode and onto the remaining uncovered portion of support 22, overlapping interconnection 18 next to cell 12′ but not contacting the adjacent oxygen electrode band 20 of cell 12′. The combination of electrolyte and interconnection closes off the porosity in the underlying support and oxygen electrode. Both electrolyte and interconnection material are disposed between inner electrodes of adjacent cells, and this is essential in this design to prevent gas leakage.

In the embodiment shown in FIG. 1, the dense electrolyte 14 overlaps the dense interconnection 18 between cells 12 and 12′ and overlaps the dense interconnection 18 near the positive terminal 26, Which latter interconnection forms a dense end portion for that device. This overlapping produces a gas impermeable barrier between the outside and the inside of the device.

Air electrode 16 from cell 12 is deposited on top of the electrolyte 14 from cell 12, continuing until contacting the interconnection 18 between cells 12 and 12′. To prevent electrical shorting between cells, a gap region is maintained between the air electrode 16 of cell 12, and the electrolyte 14 of cell 12′. These coatings of materials can be laid down by any suitable application-masking technique, such as electrochemical vapor deposition, sputtering, powder sintering, plasma arc spraying, and the like. Electrochemical vapor deposition is a preferred method of depositing electrolyte and interconnection materials, and reference may be made to U.S. Pat. No. 4,609,562 (Isenberg et al.), herein incorporated by reference, for details on that process.

This generator device is capable of generating oxygen gas from air upon application of an electrical current. Electrons from a D.C. power source (not shown) are fed into terminal 24 (negative terminal), preferably of round washer design having an extended bus bar contact area. The electrons pass through the air, electrode 16 of cell 12′, where oxygen in the air 23, which need not be pressurized, is reduced at the operating temperature of the generator, preferably heated to 650° C. to 1,100° C. by external and/or internal heating means to provide oxygen ions $O^=$, which pass through the ionically conductive, electronically non-conducting (doesn't pass $e^-$) solid oxide electrolyte 14. The oxygen ions recombine to form pure $O_2$ gas at the oxygen electrode 20 and pass through the porous support 22 into central chamber 25. The reactions are:

I. Air electrode: $O_2(\text{in air}) + 4e^- \rightarrow 2(O^=)$
II. Oxygen electrode: $2(O^=) \rightarrow O_2 + 4e^-$
III. Overall cell: $O_2(\text{in air}) \rightarrow O_2$ As shown in FIG. 1, electrons released in the oxygen electrode 20, from cell 12′, pass through interconnection 18 between cell 12 and 12′ and into the air electrode 16 of cell 12, where identical electrode reactions occur, with electrons generated in the oxygen electrode 20 from cell 12 finally passing to terminal 26 (positive terminal), of similar design as terminal 24, through the adjacent interconnection 18, and air electrode 16, and back to the D.C. power supply.

Thus, the tubular segment of interconnection material between cells provides electrical continuity (allows a flow of electrons) to the outer air electrode of a first cell of the inner oxygen electrode of a second cell, on the same device or tube, in a series arrangement. Also, air 23 is prevented from directly passing into the central chamber 25 by a continuous, dense, preferably 100% dense, barrier of electrolyte bands or segments 14 and interconnect segments 18. The dense electrolyte bands or segments 14, in part, overlap and seal to the dense interconnection segments 18. This air impermeability of the generator body is essential to providing high purity $O_2$, i.e., over approximately 95% pure, in the central chamber. While length 12 and 12′ define the "active" lengths of the two cells shown in FIG. 1 and in FIG. 2, electrode and electrolyte components shown extending out beyond the active length, are considered the active part "from" that particular cell. While the incoming air 23 does not have to be over atmospheric pressure, a great advantage in terms of the oxygen supply system, it may be pre-heated consistent with the overall system design prior to contact with the air electrodes 16 of the generator.

A variety of end closures or portions, preferably dense, can be used in the apparatus shown. In FIG. 1, the dense interconnection portion 18′, near the positive terminal, and the dense electrolyte portion 14′, near the negative terminal, are overlapped at the ends of the device and disposed transverse to the axial length of the device, as shown, to provide end closures. A high temperature resistant metal, central, axial rod, tube or the like 30, of, for example, Inconel (nickel-chromium alloy), having threads at each end, can be used in conjunction with metal end sheets 28 and 28′, to secure the sheets and the dense interconnection and electrolyte portions in a compressed relationship. As shown, one end of the rod would be screwed into a mated thread, machined into the inner side of sheet 28′, and the other end would be screwed down onto insulating rings 32 by an effective spring means (not shown), applying axial pressure to the end sheets, and assuring a gas tight fit against the flat metal terminals 24 and 26.

A suitable, high temperature resistant metal or ceramic tubular sleeve 34, having a plurality of vents or holes 36 therethrough, suitably sealed to end sheet 28, can provide oxygen delivery through the end closure 18′, as shown by the $O_2$ arrows. Inconel and alumina would both be suitable as the sleeve 34. In some instances, it may be desirable to have oxygen delivery through both ends. Alternatively, an additional hole can be drilled through end closure 18′, end air electrode 16, terminal 26 ceramic ring 32 and end sheet 28, and a tube inserted for oxygen delivery, similar to 38 in FIG. 2. The design of FIG. 1 utilizes a substantial amount of metal hardware in contact with ceramic components. There, positive and negative terminals contact air electrode material at each end of the device. The design of FIG. 2, while having more complicated terminal connections, can provide a primarily all-ceramic device, eliminating some possible problems of varying coefficients of thermal expansion between selected metals and ceramics.

Figure 2:
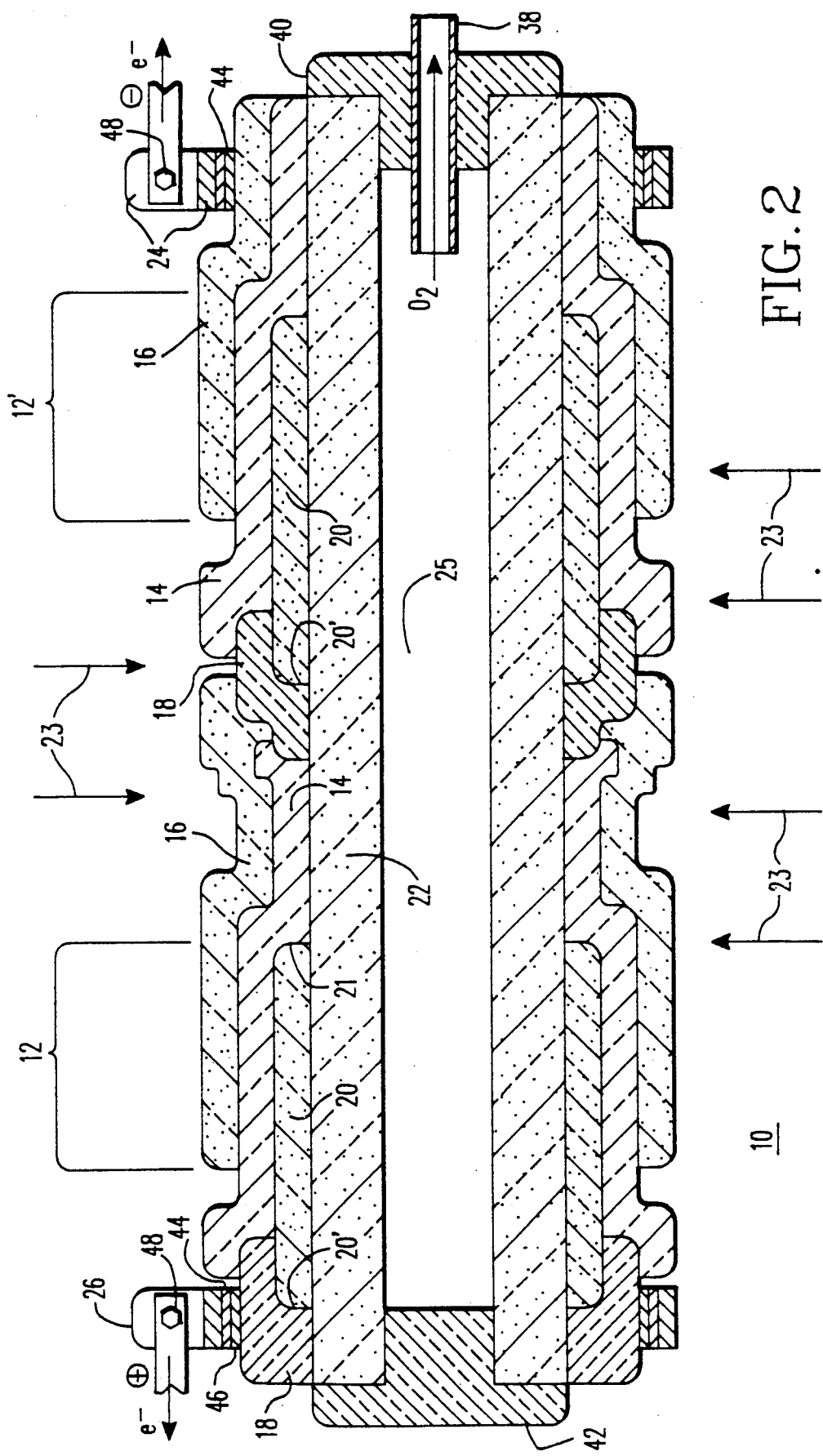
FIG. 2 shows another embodiment of the oxygen generator of this invention, in plan view partially in section.

In FIG. 2, the cell structure and interconnection between cells are essentially the same as the device of FIG. 1, utilizing the same materials and substantially the same cell connection design. However, ceramic end portions or caps 40 and 42 are used in place of the end overlapping interconnection 18′ and end overlapping electrolyte 14′ design of FIG. 1. This use requires a sinter seal comprising very fine ceramic particles (not shown) between end portions or caps 40 and 42 and the ceramic support 22. The ceramic end portions are preferably dense, to the degree of being gas impervious, and are preferably of the same material as the support tube. Preferably the ceramic support tube 22, in both embodiments, will be a zirconia material, such as stabilized zirconia, most preferably calcia-stabilized zirconia, for example $(ZrO_2)_{0.85}(CaO)_{0.15}$. This material, in pressed and highly densified form, is preferably also used as the ceramic end portions or caps 40 and 42 in FIG. 2.

Preferably, a seal (end portion or cap to support tube) is produced by squeezing a preformulated paste of very fine particle size calcia stabilized zirconia into the gap region when the end portions or caps are inserted. The ceramic end seal assembly is then dried and sintered in place, to complete fabrication. The narrow gap of the joint, the long, tortuous path, and the near-ambient pressure during operation of the device will all contribute to minimize leakage of any air into the central chamber 25 so that high purity $O_2$ can be provided. A minor amount of sintering aid, such as FeO for example, can be used in the adhesive paste and can also be used in both the support tube and end caps. Other suitable ceramic materials can also be used for the support tube, and the end caps which overlap the end of support tube 22.

While the device of FIG. 1 relies primarily on a pressure seal between overlapping end interconnection material 18', overlapping end electrolyte material 14', contacting metal terminals 24 or 26, ceramic spacers 32, and metal sheets 28 and 28', any useful high temperature adhesive can also be used between those components to assure minimal air permeation into central chamber 25.

The terminal connections on the device of FIG. 1 are of simple round washer design, having an extending bus bar contact area secured by pressure tightening rod 30, where the terminals 24 and 26 are preferably silver (m.p. 961° C.), but can also be platinum (m.p. 1,769), or palladium and alloys of palladium and platinum with silver, if the device is to be operated close to its 1,100° C. maximum operating temperature.

In the device of FIG. 2, terminal attachments are of circular band design, and directly electrically contact the top surface of the interconnection material at one end and the air electrode material at the other end of the device, and require cushioning layers. The negative terminal 24 electrically contacts the air electrode 16, preferably through a fiber metal ring 44, preferably of silver-palladium fibers. A metallic split ring clamp constitutes the terminals 24 and 26, which are shown partly in section. The terminals 24 and 26 are preferably silver-palladium alloy, but can also be solid nickel, preferably coated with silver-palladium alloy. Terminal 26 in the FIG. 2 design electrically contacts interconnection material 18 and may require an additional fiber metal ring 46, preferably of silver-palladium. Also shown in FIG. 2 are bus bar, bolt, nut, lock washer assemblies 48. Oxygen gas from the central chamber 25 shown in FIG. 2 can be delivered through tube 38, which is preferably of a ceramic such as calcia-stabilized zirconia, or by any other appropriate means at one or both ends.

Useful and approximate, non-limiting dimensions for both oxygen generator device designs are-porous support tube: 44 mm inside diameter, 50 mm outside diameter by 450 mm long; porous oxygen electrode: 15 mm long by 1 mm thick; dense interconnection: 0.1 mm to 0.5 mm thick; dense electrolyte: 11 mm long by 0.05 mm thick; and porous air electrode: 15 mm long by 0.1 mm thick. The unit would be a single stack, having a multiplicity of series-connected cells each about 1.1 cm long having an area of approximately 18 cm². For sake of simplicity, the drawings are not shown to scale.

Useful porous support tube materials, preferably from 4 mm to 10 mm thick, have been previously discussed. The oxygen electrode 20, preferably from 0.5 mm to 2 mm thick, is a 20% to 40% porous, sintered oxide material selected from doped and undoped oxides or mixtures of oxides in the pervoskite family, such as $CaMnO_3$, $LaNiO_3$, $LaCoO_3$, $LaCrO_3$, and preferably $LaMnO_3$, or other electronically conducting mixed oxides generally composed of rare earth oxides mixed with oxides of cobalt, nickel, copper, iron, chromium and manganese, and combinations of such oxides. Dopants when used are preferably selected from calcium, strontium, and magnesium, with strontium dopant preferred. The most preferred oxygen electrode is lanthanum manganite doped with strontium, for example $La_{0.9}Sr_{0.1}MnO_3$. The air electrode is preferably applied by dip slurry application and sintering.

The dense interconnection material, 18, can be selected from the group consisting of platinum-zirconia, palladium-zirconia, silver-palladium-zirconia, palladium, platinum, palladium-silver, doped lanthanum manganite, and doped lanthanum chromite. The preferred interconnection material is selected from the group consisting of doped lanthanum manganite, palladium, platinum, and palladium-silver. Dopants for the lanthanum manganite or lanthanum chromite are selected from the group consisting of calcium, strontium, and magnesium, with strontium dopant preferred. The most preferred interconnection is doped lanthanum manganite. The interconnection material is gas impervious and near 100% dense. It can be applied by well known vapor deposition techniques, and is usually from 0.05 mm to 2 mm thick. Densification can be achieved by a variety of techniques besides vapor deposition, including vapor sputtering, plasma spray, flame spray, and the like. In some cases, the interconnection, oxygen electrode, and air electrode can be the same material differing only in density and application technique, with the interconnection being the high density component.

The dense electrolyte 14, preferably from 0.02 mm to 0.15 mm thick, is a zirconia material, preferably at least 99% dense and most preferably 100% dense. The zirconia can be stabilized, that is, doped with a number of elements. Rare earth element stabilized zirconia, specifically yttria-stabilized zirconia is preferred, as it allows excellent oxygen ion mobility. A most preferred composition is $(ZrO_2)_{0.92}(Y_2O_3)_{0.08}$. Other mixed oxides can be used. The material must be effective to transfer ionic oxygen. It can be applied by chemical vapor deposition, plasma spray, flame spray, or sintering techniques.

The porous air electrode, 16, preferably from 0.05 mm to 2 mm thick, is a 20% to 60% porous material selected from metal-ceramic materials selected from the group consisting of platinum-zirconia, palladium-zirconia, and silver-palladium-zirconia, or a porous, sintered oxide selected from the group consisting of doped lanthanum manganite and doped lanthanum chromite where the preferred dopants are calcium, strontium, and magnesium, with strontium dopant preferred. Palladium-zirconia is the most preferred air electrode material. The air electrode must be effective to allow reduction of $O_2$ in air to oxygen ions.

The number of cells needed to provide a required volume of $O_2$ gas from air can be calculated. For a 3 liters/minute unit having cells of 18 cm² area, and for a driving current density of 2A/cm² and a cell current of 36A (2A/cm²×18 cm²); oxygen production per cell would be approximately 36A/cell×3.48 ml/A-min=125 ml/min-cell. If 3 liters/minute of O₂ are required, the number of cells needed would be 3000 ml O₂/min÷125 ml O₂/min-cell=24 cells/stack.

The invention will now be illustrated with reference to the following example.

EXAMPLE

A tubular electrochemical oxygen generator device, somewhat similar to that shown in FIG. 1 of the Drawings was constructed.

A 24-cell stack was built onto a 40% porous by volume calcia-stabilized zirconia tube, having an outer diameter of approximately 50 mm and a wall thickness of approximately 4 mm. A 2 mm thick oxygen electrode layer of doped lanthanum manganite was air sintered onto this zirconia tube as a continuous layer. This electrode layer was then machined into bands so that the electrode bands were electronically isolated by electrode free gaps where the zirconia tube was exposed, as shown in FIG. 1. A densified solid electrolyte segment of vapor deposited yttria-stabilized zirconia was applied over a portion of a first oxygen electrode and over the porous support tube between the first oxygen electrode and an adjacent oxygen electrode.

An air electrode, consisting of a palladium/zirconia cermet was then sintered onto the electrolyte, also forming bands, each of which contacted the oxygen electrode of an adjacent cell. To prevent electrochemical shorting between cells, a gap region was maintained between the air electrode of one cell and the electrolyte of an adjacent cell. Each cell had an electrochemically active surface area of 20 cm².

A 5-cell portion of the 24 cell stack was cut off the cell stack and end portions and electrical connections were applied, as shown in FIG. 1 and described in the specification. This 5 cell portion was tested. The device was operated at 900° C. at a current density of 2 amperes/cm², with ambient, unpressurized air delivery to the device at 5 liters/minute.

Figure 3:
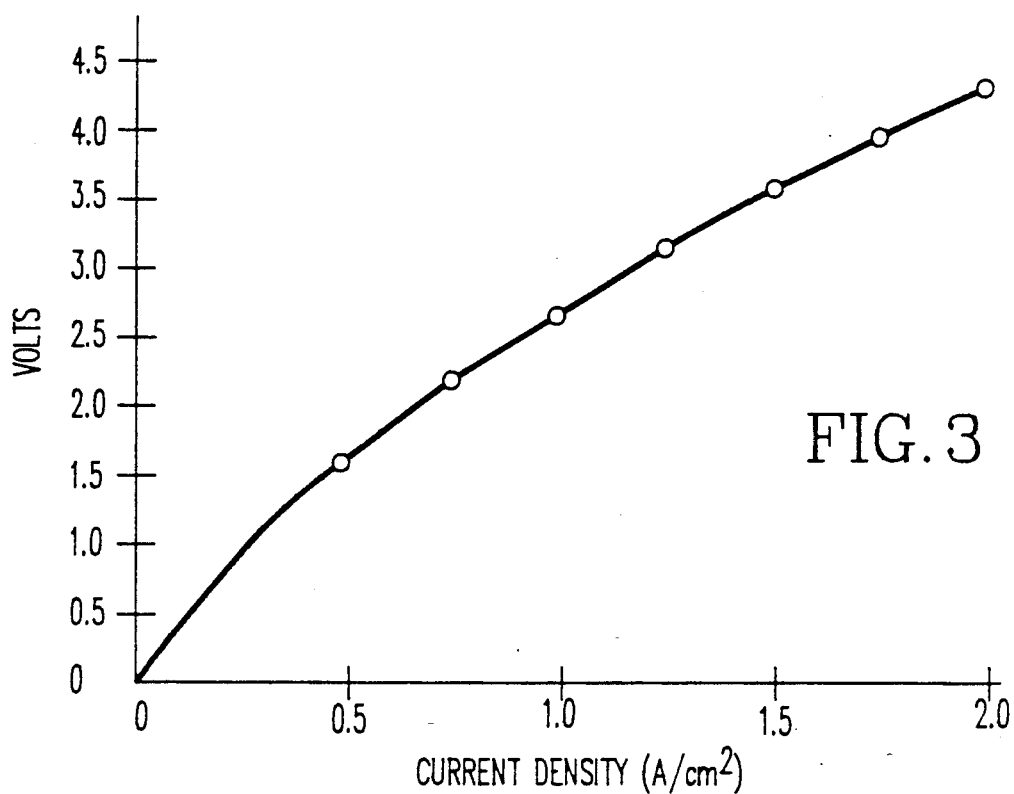
FIG. 3 shows a performance curve of voltage vs. current density for the device of the Example.
Figure 4:
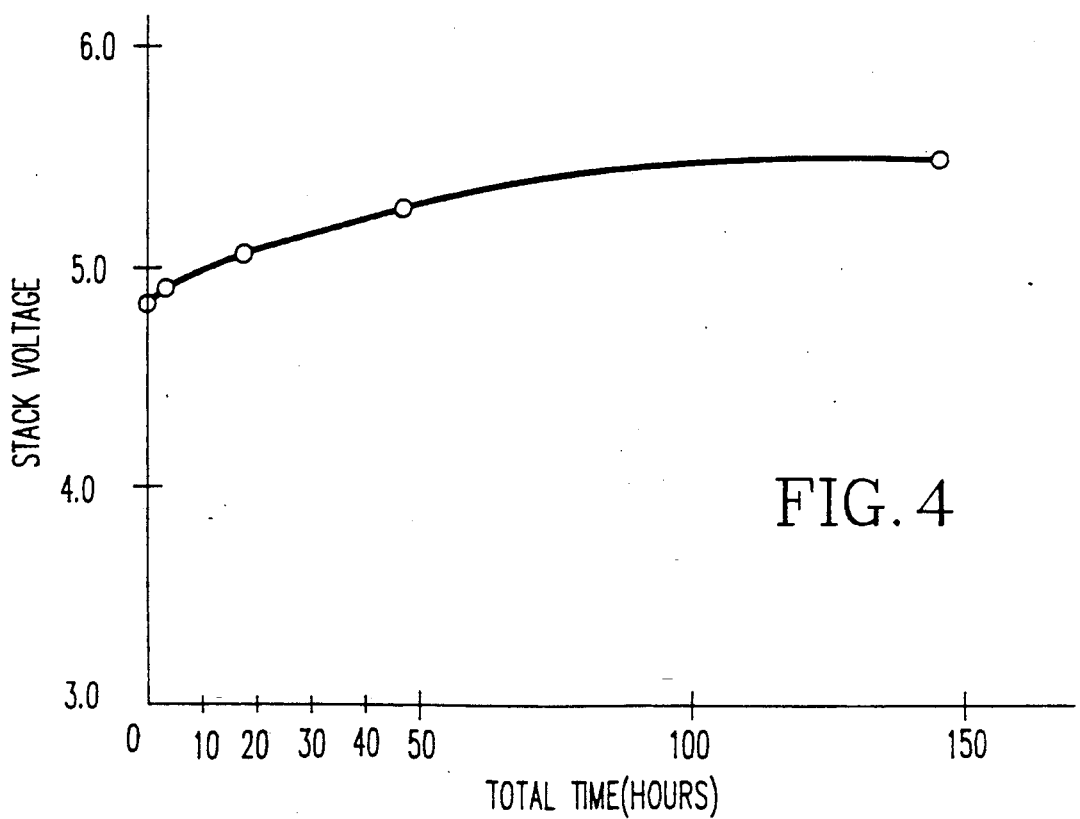
FIG. 4 shows a life performance curve of voltage vs. time for the device of the Example.

FIGS. 3 and 4 show the outstanding performance and endurance of this device under these operating conditions. The device operated at 73% extraction of the available oxygen delivered. These data show the ability of the device to operate at high current density and high rate of oxygen extraction. To insure complete gas tightness, an interconnection layer between the outer electrode of first cells and the inner electrodes of adjacent cells could easily be vapor deposited, by well known techniques, before application of electrolyte.

We claim:

1. An electrochemical device, capable of generating oxygen from air upon the application of an electrical current, comprising a plurality of adjacent electrochemical cells electrically connected in series, each cell containing an inner, porous oxygen electrode; a dense, solid oxide electrolyte capable of transporting oxygen ions partly disposed on top of the inner electrode and partly disposed between inner electrodes of adjacent cells; an outer, porous air electrode disposed on top of the electrolyte; and separate, dense, electronically conductive segments of interconnection material disposed between adjacent cells, where solid electrolyte between adjacent cells contacts part of the interconnection to provide a dense, gas impermeable barrier between the outside and the inside of the device, with the interconnection electrically and physically connecting the outer air electrode from one cell, to the inner oxygen electrode from an adjacent cell, to provide a device having gas impermeable, dense, contacting segments of electrolyte and interconnection material between inner electrodes of adjacent cells, and where the device contains positive and negative terminals, the negative terminal being effective to allow feeding of current into a contacting air electrode.

2. The electrochemical device of claim 1, where the inner oxygen electrode is disposed on a porous support tube, the support tube, oxygen electrode, electrolyte, interconnection material, and air electrode are all of continuous tubular construction, and the device contains two end portions; at least one of which provides for oxygen delivery.

3. The electrochemical device of claim 2, where the end portions are a dense layer of interconnection material on one end and a dense layer of electrolyte material on the other end of the device, disposed transverse to the axial length of the device, secured in a compressed relationship by a central axial rod, and where positive and negative electrical terminals contact air electrode material at each end of the device.

4. The electrochemical device of claim 2, where the end portions are two dense, sintered-in-place ceramic caps, and where the positive terminal electrically contacts interconnection material at one end of the device and the negative terminal electrically contacts air electrode material at the other end of the device.

5. The electrochemical device of claim 1, where the inner oxygen electrode contains a porous, sintered oxide; the electrolyte contains a dense, zirconia material; the interconnetion material contains dense, electronically conductive material; and the air electrode is selected from the group consisting of porous, metal-ceramic material and porous, sintered oxide.

6. The electrochemical device of claim 1, where the interconnection material consists essentially of dense, electronically conductive material selected from the group consisting of platinum-zirconia, palladium-zirconia, silver-palladium-zirconia, palladium, platinum, palladium-silver, doped lanthanum manganite, and doped lanthanum chromite.

7. The electrochemical device of claim 1, where the air electrode is an exterior electrode effective to allow formation of oxygen ions from O₂ upon application of a current, and consists essentially of a porous material selected from the group consisting of platinum-zirconia, palladium-zirconia, silver-palladium-zirconia, doped lanthanum manganite and doped lanthanum chromite, where the solid electrode from the first cell continues beyond the end of the oxygen electrode of the first cell to overlap part of the interconnection, and where the oxygen electrode is an interior electrode effective to allow oxygen ion recombination to form O₂.

8. The electrochemical device of claim 1, where electrical current can be fed into and through the cells, where air ca contact the outer electrodes and electrolyte but cannot permeate through the dense contacting segments of electrolyte and interconnection material, and where oxygen from the air can be transported in ionic form across the electrolyte to provide oxygen gas within the device.

9. The electrochemical device of claim 8, operating at a temperature of from 650° C. to 1,100° C., where current is fed into and through the cells, air contacts the outer air electrode and oxygen from the air, as oxygen ions, is transported across the electrolyte to form oxygen gas within the device.

10. The electrochemical device of claim 1, driven by a D.C. power source, and operating at from 650° C. to 1,100° C. with air.

11. The electrochemical device of claim 1, operating at from 650° C. to 1,100° C. with at least one of external heating means or internal heating means.

12. The electrochemical device of claim 1, where the inner oxygen electrode is disposed on a porous support tube; the support tube, oxygen electrode, electrolyte, interconnection material, the air electrode are all of tubular construction; the device contains two end portions, at least one of which provides for oxygen delivery, disposed transverse to the axial length of the device and secured in a compressed relationship by a central axial rod; and where said device is operating at from 650° C. to 1,100° C. with air.

13. An electrochemical device, capable of generating oxygen from air upon the application of an electrical current, comprising a plurality of adjacent electrochemical cells electrically connected in series, each cell containing an inner, porous oxygen electrode; a dense, solid oxide electrolyte capable of transporting oxygen ions partly disposed on top of the inner electrode and partly disposed between inner electrodes of adjacent cells; an outer, porous air electrode disposed on top of the electrolyte; and separate, dense, electronically conductive segments of interconnection material disposed between adjacent cells, where the inner oxygen electrode of a first cell and the inner oxygen electrode of an adjacent cell are separated from each other and disposed on a porous support, interconnection material contacts part of the uncovered portion of the support next to the oxygen electrode of the adjacent cell and contacts a portion of that oxygen electrode, and the solid electrolyte from the first cell continues beyond the end of the oxygen electrode of the first cell onto the remaining uncovered portion of the support, contacting part of the interconnection to provide a dense, gas impermeable barrier between the outside and the inside of the device, with the interconnection electrically and physically connecting the outer air electrode from one cell, to the inner oxygen electrode from an adjacent cell, to provide a device having gas impermeable, dense, contacting segments of electrolyte and interconnection material between inner electrodes of adjacent cells.

14. The electrochemical device of claim 13, where the device contains two end portions; at least one of which provides for oxygen delivery.

15. The electrochemical device of claim 13, where the end portions are a dense layer of interconnection material on one end and a dense layer of electrolyte material on the other end of the device, disposed transverse to the axial length of the device, and secured in a compressed relationship by a central axial rod, and where positive and negative electrical terminals contact air electrode material at each end of the device.

16. The electrochemical device of claim 13, where the end portions are two dense, sintered-in-place ceramic caps, and where the positive terminal electrically contacts interconnection material at one end of the device and the negative terminal electrically contacts air electrode material at the other end of the device.

17. The electrochemical device of claim 13, driven by a D.C. power source, and operating at from 650° C. to 1,100° C. with air.

18. The electrochemical device of claim 13, operating at from 650° C. to 1,100° C. with at least one of external heating means or internal heating means.

19. The electrochemical device of claim 13, were the interconnection material overlaps a portion of oxygen electrode and the electrolyte from the first cell overlaps part of the interconnection, the support tube, oxygen electrode, electrolyte, interconnection material, and air electrode are all of tubular construction; the device contains two end portions, at least one of which provides for oxygen delivery, disposed transverse to the axial length of the device, and secured in a compressed relationship by a central axial rod; and where said device is operating at from 650° C. to 1,100° C. with air.

20. An electrochemical device, capable of generating oxygen from air upon the application of an electrical current, comprising a plurality of adjacent tubular electrochemical cells electrically connected in series, each cell containing a tubular, porous support tube; an inner, tubular, porous oxygen electrode disposed on the support tube; a tubular, dense, solid oxide electrolyte capable of transporting oxygen ions partly disposed on top of the inner electrode and partly disposed between inner electrodes of adjacent cells; an outer, tubular, porous air electrode disposed on top of the electrolyte; and separate, dense, electronically conductive, tubular segments of interconnection material disposed between adjacent cells, where the inner oxygen electrode of a first cell and the inner oxygen electrode of an adjacent cell are separated from each other and disposed on a porous support tube, interconnection material contacts part of the uncovered portion of the support next to the oxygen electrode of the adjacent cell and overlaps a portion of that oxygen electrode, and the solid electrolyte from the first cell continues beyond the end of the oxygen electrode of the first cell onto the remaining uncovered portion of the support, overlapping part of the interconnection to provide a dense, gas barrier between the outside and the inside of the device, with the interconnection electrically and physically connecting the outer air electrode from one cell, to the inner oxygen electrode from an adjacent cell, where the interconnection material is selected from the group consisting of platinum-zirconia, palladium-zirconia, silver-palladium-zirconia, palladium, platinum, palladium-silver, doped lanthanum manganite, and doped lanthanum chromite, and the air electrode is a porous material selected from the group consisting of platinum-zirconia, palladium-zirconia, silver-palladium-zirconia, doped lanthanum manganite and doped lanthanum chromite, to provide a device having gas impermeable, dense, contacting segments of electrolyte and interconnection material between inner electrodes of adjacent cells, said device also having two end portions, at least one of which provides for oxygen delivery, and electrical terminals.

21. The electrochemical device of claim 20, whre the inner oxygen electrode contains porous, doped lanthanum manganite, and the electrolyte contains dense, stabilized zirconia.

22. The electrochemical device of claim 20, where the end portions are a dense layer of interconnection material on one end and a dense layer of electrolyte material on the other end of the device, disposed transverse to the axial length of the device, secured in a compressed relationship by a central axial rod, and where positive and negative electrical terminals contact air electrode material at each end of the device.

23. The electrochemical device of claim 20, where the end portions are two dense, sintered-in-place ceramic caps, and where the positive terminal electrically contacts interconnection material at one end of the device and the negative terminal electrically contacts air electrode material at the other end of the device.

24. A high temperature electrochemical device, capable of generating oxygen from air upon the application of an electrical current, comprising a plurality of adjacent tubular electrochemical cells electrically connected in series, each cell containing a tubular, porous support tube; an inner, tubular, porous oxygen electrode disposed on the support tube; a tubular, dense, solid oxide electrolyte capable of transporting oxygen ions disposed on top of the inner electrode; an outer, tubular, porous air electrode disposed on top of the electrolyte; and separate, dense, electronically conductive, tubular segments of interconnection material disposed between adjacent cells, where the inner oxygen electrode of a first cell and the inner oxygen electrode of an adjacent cell are separated from each other and disposed on a porous support tube, interconnection material contacts part of the uncovered portion of the support next to the oxygen electrode of the adjacent cell and overlaps a portion of that oxygen electrode, and the solid electrolyte from the first cell continues beyond the end of the oxygen electrode of the first cell onto the remaining uncovered portion of the support, overlapping part of the interconnection to provide a dense, gas impermeable barrier between the outside and the inside of the device, with the interconnection electrically and physically connecting the outer air electrode from one cell, to the inner oxygen electrode from an adjacent cell, to provide a device having gas impermeable, dense, contacting segments of electrolyte and interconnection material, said device also having two end portions, at least one of which provides for oxygen delivery, where said device is operating at a temperature of from 650° C. to 1,100° C., current is fed into and through the cells, air contacts the outer electrode and oxygen from the air, as oxygen ions, is transported across the electrolyte to form oxygen gas within the device.

25. The electrochemical device of claim 24, where the electrolyte is partly disposed on top of the inner electrode and partly disposed between inner electrodes of adjacent cells, the air is unpressurized, the interconnection material is selected from the group consisting of platinum-zirconia, palladium-zirconia, silver-palladium-zirconia, palladium, platinum, palladium-silver, doped lanthanum manganite and doped lanthanum chromite, and the air electrode is a porous material selected from the group consisting of platinum-zirconia, palladium-zirconia, silver-palladium-zirconia, doped lanthanum manganite, and doped lanthanum chromite.

26. The electrochemical device of claim 24, where the inner oxygen electrode contains porous, doped lanthanum manganite, and the electrolyte contains dense, stabilized zirconia.

27. The electrochemical device of claim 24, where the end portions are a dense layer of interconnection material on one end and a dense layer of electrolyte material on the other end of the device, disposed transverse to the axial length of the device, secured in a compressed relationship by a central axial rod, and where positive and negative electrical terminals contact air electrode material at each end of the device.

28. The electrochemical device of claim 24, where the end portions are two dense, sintered-in-place ceramic caps, and where the positive terminal electrically contacts interconnection material at one end of the device and the negative terminal electrically contacts air electrode material at the other end of the device.

29. An electrochemical device, capable of generating oxygen from air upon the application of an electrical current, comprising a plurality of adjacent electrochemical cells electrically connected in series, each cell containing an inner, porous oxygen electrode; a dense, solid oxide electrolyte partly disposed on top of the inner electrode; an outer, porous air electrode disposed on top of the electrolyte; and separate, dense, electronically conductive segments of interconnection material disposed between adjacent cells, where solid electrolyte and interconnection contact between adjacent cells to provide a dense, gas impermeable barrier between the outside and inside of the device, with the interconnection electrically and physically connecting the outer air electrode from one cell, to the inner oxygen electrode from an adjacent cell, and where the device contains positive and negative terminals, the negative terminals being effective to allow feeding current into a contacting air electrode.

30. The electrochemical device of claim 29, where the inner oxygen electrode is disposed on a porous support tube, the support tube, oxygen electrode, electrolyte, interconnection material, and air electrode are all of continuous tubular construction, and the device contains two end portions; at least one of which provides for oxygen delivery.

31. The electrochemical device of claim 29, where the air electrode is an exterior electrode effective to allow formation of oxygen ions from $O_2$ upon application of a current, and consists essentially of a porous material selected from the group consisting of platinum-zirconia, palladium-zirconia, silver-palladium-zirconia, doped lanthanum manganite and doped lanthanum chromite, where the solid electrode from the first cell continues beyond the end of the oxygen electrode of the first cell to overlap part of the interconnection, and where the oxygen electrode is an interior electrode effective to allow oxygen ion recombination to form $O_2$.

32. The electrochemical device of claim 29, driven by a power source, and operating up to 1,100° C. with air.

* * * * *